United States Patent [19]

Rosenberger et al.

[11] Patent Number: 4,855,345
[45] Date of Patent: Aug. 8, 1989

[54] STABILIZERS FOR ORGANIC POLYMERS

[75] Inventors: Siegfried Rosenberger, Riehen; Hans-Rudolf Meier, Marly, both of Switzerland

[73] Assignee: Ciba-Geigy Corporation, Ardsley, N.Y.

[21] Appl. No.: 60,287

[22] Filed: Jun. 10, 1987

[30] Foreign Application Priority Data

Jun. 19, 1986 [CH] Switzerland .................... 2483/86

[51] Int. Cl.[4] ............................. C08K 5/49; C07F 9/15
[52] U.S. Cl. ...................................... 524/120; 558/78; 558/85; 558/194; 524/119; 524/117
[58] Field of Search ................ 558/85, 78, 194; 524/119, 120, 117

[56] References Cited

U.S. PATENT DOCUMENTS 2,847,443 8/1958 Hechenbleikner et al. ......... 558/118
4,513,109 4/1985 Rosenberger ...................... 568/720

FOREIGN PATENT DOCUMENTS 250367 12/1987 European Pat. Off. ............ 558/78
146959 3/1981 German Democratic Rep. .

OTHER PUBLICATIONS

H. J. Lucas, et al., J. Am. Chem. Soc., 72, 5491 (1950).
Unvarified Translation of Japanese, 128044, 12/7/74.

Primary Examiner—Anton H. Sutto
Attorney, Agent, or Firm—Luther A. R. Hall

[57] ABSTRACT

Compounds of the formula I

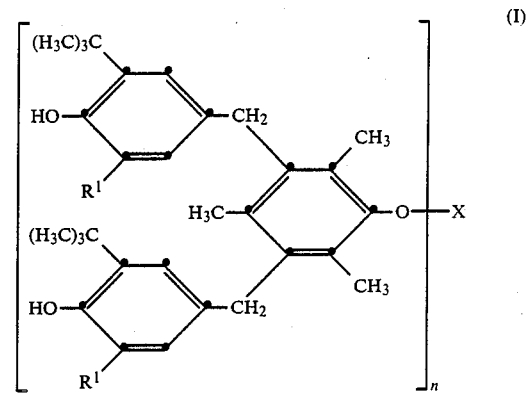

in which n is 1, 2 or 3, $R^1$ is $C_1$–$C_5$-alkyl, cyclohexyl or α-methylcyclohexyl and, if n is 1, X is a group of the formula II or III

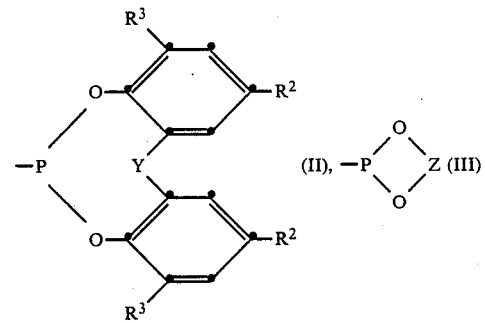

in which $R^2$ and $R^3$ independently of one another are $C_1$–$C_8$-alkyl or cyclohexyl, Y is a direct bond, —S—, >S=O or a radical —$CR^4R^5$— in which $R^4$ is hydrogen, $C_1$–$C_8$-alkyl, $C_5$–$C_8$-cycloalkyl, phenyl or benzyl and $R^5$ is hydrogen or $C_1$–$C_8$-alkyl, and Z is 1,2-alkylene or 1,3-alkylene having not more than 15 carbon atoms or o-phenylene, and, if n is 2, X is a group of the formula IV or V

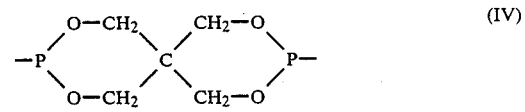

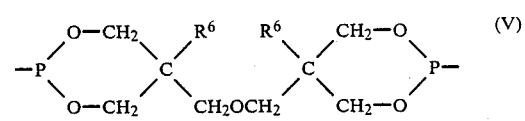

in which $R^6$ is methyl or ethyl, and, if n is 3, X is a phosphorus atom, are suitable for stabilizing organic material against light-induced and/or thermo-oxidative degradation.

11 Claims, No Drawings

STABILIZERS FOR ORGANIC POLYMERS

The present invention relates to novel sterically hindered phosphites, their use for stabilizing organic material and the organic material which has been stabilized by means of them against thermo-oxidative and/or light-induced degradation.

Phosphites of pentaerythritol and the use thereof for stabilizing vinyl and vinylidene resins are disclosed in U.S. Pat. No. 2,847,443. Japanese Published Specification 74-128,044 describes polypropylene compositions containing a sterically hindered phosphite of pentaerythritol and a metal soap.

The invention relates to compounds of the formula I

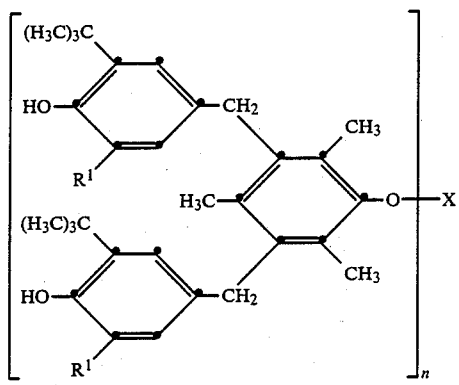

in which n is 1, 2 or 3, $R^1$ is $C_1$–$C_5$-alkyl, cyclohexyl or α-methylcyclohexyl and, if n is 1, X is a group of the formula II or III

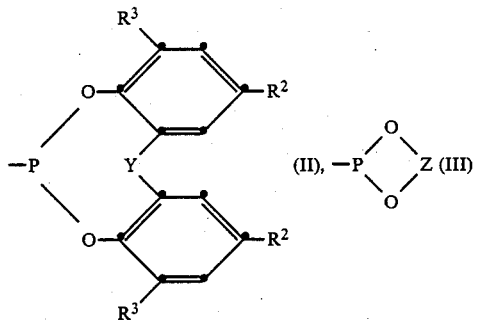

in which $R^2$ and $R^3$ independently of one another are $C_1$–$C_8$-alkyl or cyclohexyl, Y is a direct bond, —S—, >S=O or a radical —$CR^4R^5$— in which $R^4$ is hydrogen, $C_1$–$C_8$-alkyl, $C_5$–$C_8$-cycloalkyl, phenyl or benzyl and $R^5$ is hydrogen or $C_1$–$C_8$-alkyl, and Z is 1,2-alkylene or 1,3-alkylene having not more than 15 carbon atoms or o-phenylene, and, if n is 2, X is a group of the formula IV or V

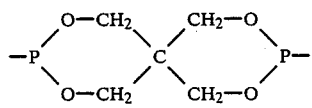

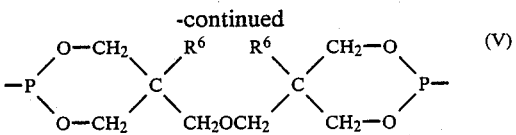

in which $R^6$ is methyl or ethyl, and, if n is 3, X is a phosphorus atom.

Examples of $R^1$ as $C_1$–$C_5$-alkyl are methyl, ethyl, propyl, isopropyl, butyl, isobutyl, tert.-butyl, pentyl or isopentyl. Methyl and tert.-butyl are preferred, and tert.-butyl is particularly preferred.

As $C_1$–$C_8$-alkyl, $R^2$, $R^3$, $R^4$ and $R^5$ can, for example, be as defined above for $R^1$ and can additionally be hexyl, heptyl, octyl or isooctyl. $C_1$–$C_4$-alkyl is preferred. It is particularly preferable for $R^2$ and $R^3$ to be methyl or tert.-butyl.

Examples of $R^4$ as $C_5$–$C_8$-cycloalkyl are cyclopentyl, cyclohexyl, cycloheptyl or cyclooctyl. Cyclohexyl is preferred.

The following may be mentioned as examples of the group Z, which, together with the phosphorus atom and the two oxygen atoms, forms a 5-membered or 6-membered ring: 1,2-ethylene, 1,2-propylene, 1,3-propylene, 1,2-butylene, tetramethyl-1,2-ethylene, 2,2-dimethyl-1,3-propylene, 2-methyl-2-ethyl-1,3-propylene, 1,1,3-trimethyl-1,3-propylene, 1-propyl-2,2-dimethyl-1,2-ethylene and 1-propyl-2,2-dimethyl-1,3-propylene. Z is preferably a branched 1,2-alkylene or 1,3-alkylene group having not more than 8 carbon atoms. A 1,3-alkylene group is particularly preferred, especially 2,2-dimethyl-1,3-propylene and 1-propyl-2,2-dimethyl-1,3-propylene.

Compounds of the formula I which are of interest are those in which n is 1, 2 or 3, $R^1$ is methyl, tert.-butyl or cyclohexyl and, if n is 1, X is a group of the formula II or III in which Y is a direct bond, —S— or —$CR^4R^5$— in which $R^4$ and $R^5$ independently of one another are hydrogen or $C_1$–$C_4$-alkyl, and Z is 1,2-alkylene or 1,3-alkylene having not more than 8 carbon atoms.

Compounds of the formula I which are of particular interest are those in which n is 1, 2 or 3, $R^1$ is methyl or tert.-butyl and, if n is 1, X is a group of the formula II or III in which $R^2$ and $R^3$ independently of one another are $C_1$–$C_4$-alkyl and $R^3$ is additionally cyclohexyl, Y is —S—, —$CH_2$— or —$CH(C_1$–$C_4$-alkyl)— and Z is a 1,3-alkylene group which has 4 to 8 carbon atoms and is branched in the 2-position.

Compounds of the formula I which are preferred are those in which n is 1, 2 or 3 and, if n is 1, X is a group of the formula II and, if n is 2, X is a group of the formula IV.

Compounds of the formula I which are particularly preferred are those in which n is 1, 2 or 3 and, if n is 1, X is a group of the formula II or III in which Y is —S—, —$CH_2$— or —$CHCH_3$— and Z is a 1,3-alkylene group which has 4 to 8 carbon atoms and is branched in the 2-position.

Compounds of the formula I which are also of interest are those in which n is 1, 2 or 3, $R^1$ is $C_1$–$C_4$-alkyl and, if n is 1, X is a group of the formula II or III in which $R^2$ and $R^3$ independently of one another are $C_1$–$C_4$-alkyl, Y is —$CH_2$— and Z is a 1,3-alkylene group which has 4 to 8 carbon atoms and is branched in the 2-position, and, if n is 2, X is a group of the formula IV.

n is preferably 1 or 2.

The following are examples of compounds of the formula I (a) 3,9-bis-[3',5'-bis-(3'',5''-ditert.-butyl-4''-hydroxybenzyl)-2',4',6'-trimethylphenoxy]-2,4,8,10-tetraoxa-3,9-diphosphaspiro[5,5]undecane (b) 3,9-bis-[3',5'-bis-(3''-tert.-butyl-5''-methyl-4''-hydroxybenzyl)-2',4',6'-trimethylphenoxy]-2,4,8,10-tetraoxa-3,9-diphosphaspiro[5,5]undecane (c) 3,9-bis-[3',5'-bis-(3''-tert.-butyl-5''-cyclohexyl-4''-hydroxybenzyl)-2',4',6'-trimethylphenoxy]-2,4,8,10-tetraoxa-3,9-diphosphaspiro[5,5]undecane (d) 2-[3',5'-bis-(3'',5''-ditert.-butyl-4''-hydroxybenzyl)-2',4',6'-trimethylphenoxy]-5,5-dimethyl[1,3,2]dioxaphosphinane (e) 2-[3',5'-bis-(3''-tert.-butyl-5''-methyl-4''-hydroxybenzyl)-2',4',6'-trimethylphenoxy]-5,5-dimethyl[1,3,2]dioxaphosphinane (f) 2-[3',5'-bis-(3'',5''-ditert.-butyl-4''-hydroxybenzyl)-2',4',6'-trimethylphenoxy]-2,4,8,10-tetra-tert.-butyl-dibenzo[d,g][1,3,2]dioxaphosphocin (g) 2-[3',5'-bis-(3'',5''-ditert.-butyl-4''-hydroxybenzyl)-2',4',6'-trimethylphenoxy]-2,4,8,10-tetramethyl-dibenzo[d,g][1,3,2]dioxaphosphocin (h) 2-[3',5'-bis-(3''-tert.-butyl-5''-methyl-4''-hydroxybenzyl)-2',4',6'-trimethylphenoxy]-2,4,8,10-tetra-tert.-butyl-dibenzo[d,g][1,3,2]dioxaphosphocin (i) 2-[3',5'-bis-(3''-tert.-butyl-5''-methyl-4'''-hydroxybenzyl)-2',4'',6'-trimethylphenoxy]-2,4,8,10-tetramethyl-dibenzo[d,g][1,3,2]dioxaphosphocin (j) 2-[3',5'-bis-(3'',5''-ditert.-butyl-4''-hydroxybenzyl)-2',4',6'-trimethylphenoxy]-2,10-dimethyl-4,8-dicyclohexyl-dibenzo[d,g][1,3,2]dioxaphosphocin (k) 2-[3',5'-bis-(3'',5''-ditert.-butyl-4''-hydroxybenzyl)-2',4',6'-trimethylphenoxy]-2,10-dimethyl-4,8-ditert.-butyl-dibenzo[d,g][1,3,2]dioxaphosphocin (l) 2-[3',5'-bis-(3'',5''-ditert.-butyl-4''-hydroxybenzyl)-2',4',6'-trimethylphenoxy]-2,4,8,10-tetra-tert.-butyl-dibenzo[d,g][1,3,2,6]dioxaphosphathiocin (m) 2-[3',5'-bis-(3'',5''-ditert.-butyl-4''-hydroxybenzyl)-2',4',6'-trimethylphenoxy]-2,10-dimethyl-4,8-ditert.-butyl-dibenzo[d,g][1,3,2,6]dioxaphosphathiocin (n) 2-[3',5'-bis-(3'',5''-ditert.-butyl-4''-hydroxybenzyl)-2',4',6'-trimethylphenoxy]-2,10-dimethyl-4,8-ditert.-butyl-12-methyl-dibenzo[d,g][1,3,2]dioxaphosphocin (o) tris[3,5-bis-(3',5'-ditert.-butyl-4'-hydroxybenzyl)-2,4,6-trimethylphenyl]phosphite (p) tris[3,5-bis-(3',5'-ditert.-butyl-4'-hydroxybenzyl)-2,4,6-trimethylphenyl]phosphite Compounds (a), (d), (f), (k) and (p) are particularly preferred.

The compounds of the formula I in which n is 1 or 2 can be prepared analogously to known processes; for example by reacting n mol of a phenol of the formula VI

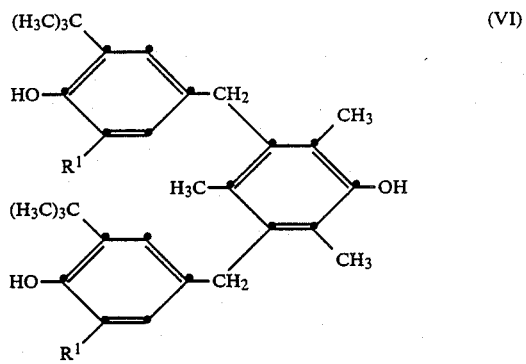

in which $R^1$ is as defined above with one mol of a chlorophosphite of the formula VII

in which X is as defined above and n is 1 or 2, in an organic solvent, in the presence of a basic catalyst and at a temperature between 0° C. and the boiling point of the solvent used. Examples of organic solvents which can be used are chlorinated hydrocarbons, aromatic hydrocarbons, for example toluene or xylene, or polar, aprotic solvents, for example dimethylformamide. Examples of suitable basic catalysts are alkali and alkaline earth metal hydroxides, alkali and alkaline earth metal carbonates and tertiary amines, preferably pyridine and trialkylamines, for example trimethylamine, triethylamine and tributylamine. It is advantageous to employ the base in at least the equivalent amount required to remove the hydrogen chloride formed during the reaction. The reaction time can, for example, be 2 to 30 hours. When the reaction is complete, the salts which have been formed from the base employed and the hydrogen chloride set free during the reaction can be filtered off. After the solvent has been removed it is appropriate to work up the crude product by customary methods (for example recrystallization or column chromatography).

In a variant of the above process of preparation it is also possible to employ an alkali metal salt of the compound of the formula VI or a mixture of a compound of the formula VI and an alkali metal salt thereof. It is appropriate to employ, as alkali metal salts, the lithium, sodium and potassium salts of the phenol of the formula VI.

The compounds of the formula I in which n is 3 can be prepared analogously to the process described above by reacting 3 mol of a phenol of the formula VI or an alkali metal salt thereof with one mol of $PCl_3$.

The starting materials of the formula VI are known (in some cases commercially available) and can be prepared analogously to known processes, for example as described in U.S. Pat. No. 4,513,109.

The chlorophosphites of the formula VII are also known and can be prepared from the corresponding diols and $PCl_3$ as described, for example, in J. Am. Chem. Soc. 72, 5491–7 (1950).

The compounds of the formula I are suitable for stabilizing organic materials against light-induced and/or thermo-oxidative degradation. The following are examples of materials of this type:

1. Polymers of monoolefins and diolefins, for example polypropylene, polyisobutylene, polybut-1-ene, polymethylpent-1-ene, polyisoprene or polybutadiene, and polymers of cyclo-olefins, for example those of cyclopentene or norbornene; and also polyethylene (which can, if appropriate, be cross-linked), for example high-density polyethylene (HDPE), low-density polyethylene (LDPE) and linear, low-density polyethylene (LLDPE).

2. Mixtures of the polymers mentioned under (1), for example mixtures of polypropylene with polyisobutylene and of polypropylene with polyethylene (for example PP/HDPE and PP/LDPE) and mixtures of different types of polyethylene (for example LDPE/HDPE).

3. Copolymers of monoolefins and diolefins with one another or with other vinyl monomers, for example ethylene/propylene copolymers, linear, low-density polyethylene (LLDPE) and mixtures thereof with low-density polyethylene (LDPE), propylene/but-1-ene copolymers, propylene/isobutylene copolymers, ethylene/but-1-ene copolymers, ethylene/hexene copolymers, ethylene-methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers or ethylene/acrylic acid copolymers and salts thereof (ionomers) and terpolymers of ethylene with propylene and a diene, such as hexadiene, dicyclopentadiene and ethylidenenorbornene; also mixtures of such copolymers with one another and with polymers mentioned under (1), for example polypropylene-ethylene/propylene copolymers, LDPE-ethylene/vinyl acetate copolymers, LDPE-ethylene/acrylic acid copolymers, LLDPE-ethylene/vinyl acetate copolymers and LLDPE-ethylene/acrylic acid copolymers.

3a. Hydrocarbon resins (for example $C_5$–$C_9$), including hydrogenated modifications thereof (for example tackifier resins).

4. Polystyrene, poly-(p-methylstyrene) and poly-(α-methylstyrene).

5. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/maleic anhydride and styrene/acrylonitrile/methyl acrylate; mixtures of high impact strength formed from styrene copolymers and another polymer, for example a polyacrylate, a diene polymer or an ethylene/propylene/diene terpolymer, and block copolymers of styrene, for example styrene/butadiene/styrene, styrene/isoprene/styrene, styrene/ethylene-butylene/styrene or styrene/ethylene-propylene/styrene.

6. Graft copolymers of styrene or α-methylstyrene, for example styrene on polybutadiene, styrene on polybutadiene/styrene or polybutadiene/acrylonitrile copolymers, and styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene, styrene and maleimide on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers, and mixtures thereof with the copolymers mentioned under (5), such as are known, for example, as so-called ABS, MBS, ASA or AES polymers.

7. Halogen-containing polymers, for example polychloroprene, chlorinated rubber, chlorinated or chlorosulfonated polyethylene, epichlorohydrin homopolymers and copolymers, in particular polymers formed from halogen-containing vinyl compounds, for example polyvinyl chloride, polyvinylidene chloride, polyvinyl fluoride and polyvinylidene fluoride; and copolymers thereof, such as vinyl chloride/vinylidene chloride, vinyl chloride/vinyl acetate or vinylidene chloride/vinyl acetate.

8. Polymers derived from α,β-unsaturated acids and derivatives thereof, such as polyacrylates and polymethacrylates, polyacrylamides and polyacrylonitriles.

9. Copolymers of the monomers mentioned under (8) with one another or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

10. Polymers derived from unsaturated alcohols and amines or acyl derivatives or acetals thereof, such as polyvinyl alcohol, polyvinyl acetate, stearate, benzoate or maleate, polyvinyl butyral, polyallyl phthalate and polyallylmelamine; and copolymers thereof with olefins mentioned in item 1.

11. Homopolymers and copolymers of cyclic ethers, such as polyalkylene glycols, polyethylene oxide, polypropylene oxide or copolymers thereof with bisglycidyl ethers.

12. Polyacetals, such as polyoxymethylene and polyoxymethylenes containing comonomers, for example ethylene oxide; and polyacetals which have been modified with thermoplastic polyurethanes, acrylates or MBS.

13. Polyphenylene oxides and sulfides and mixtures thereof with styrene polymers or polyamides.

14. Polyurethanes derived on the one hand from polyethers, polyesters and polybutadienes having terminal hydroxyl groups and from aliphatic or aromatic polyisocyanates on the other hand, and also precursors thereof.

15. Polyamides and copolyamides derived from diamines and dicarboxylic acids and/or from aminocarboxylic acids or the corresponding lactams, such as polyamide 4, polyamide 6, polyamide 6/6, 6/10, 6/9, 6/12 or 4/6, polyamide 11, polyamide 12, aromatic polyamides obtained from m-xylylenediamine and adipic acid; polyamides prepared from hexamethylenediamine and isophthalic and/or terephthalic acid and, if appropriate, and elastomer as modifier, for example poly-2,4,4-trimethylhexamethyleneterephthalamide or poly-m-phenyleneisophthalamide. The block copolymers of the polyamides mentioned above with polyolefins, olefin copolymers, ionomers or chemically linked or grafted elastomers; or with polyethers, for example polyethylene glycol, polypropylene glycol or polytetramethylene glycol. Also polyamides or copolyamides modified with EPDM or ABS; and polyamides subjected to condensation during processing ("RIM-polyamide systems").

16. Polyureas, polyimides, polyamide-imides and polybenzimidazoles.

17. Polyesters derived from dicarboxylic acids and dialcohols and/or from hydrocarboxylic acids or the corresponding lactones, such as polyethylene terephthalate, polybutylene terephthalate, poly-1,4-dimethylolcyclohexane terephthalate, polyhydroxybenzoates and block polyether-esters derived from polyethers containing hydroxyl end groups; also polyesters modified with polycarbonates or MBS.

18. Polycarbonates and polyester-carbonates.

19. Polysulfones, polyether-sulfones and polyether-ketones.

20. Crosslinked polymers derived on the one hand from aldehydes and on the other hand from phenols, urea or melamine, such as phenol/formaldehyde, urea-/formaldehyde and melamine/formaldehyde resins.

21. Drying and non-drying alkyd resins.

22. Unsaturated polyester resins derived from copolyesters of saturated and unsaturated dicarboxylic acids with polyhydric alcohols, and also vinyl compounds as crosslinking agents and also halogen-containing, low-flammability modifications thereof.

23. Crosslinkable acrylic resins derived from substituted acrylic acid esters, for example epoxy-acrylates, urethane-acrylates or polyester-acrylates.

24. Alkyd resins, polyester resins and acrylate resins which have been crosslinked with melamine resins, urea resins, polyisocyanates or epoxide resins.

25. Crosslinked epoxide resins derived from polyepoxides, for example bisglycidyl ethers or cycloaliphatic diepoxides.

26. Natural polymers, such as cellulose, natural rubber, gelatin and polymer-homologously chemically modified derivatives thereof, such as cellulose acetates, propionates and butyrates, and the cellulose ethers, such as methyl cellulose; and colophony resins and derivatives.

27. Mixtures (polyblends) of the abovementioned polymers, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP and PA/PPO.

28. Natural and synthetic organic materials constituting pure monomeric compounds or mixtures thereof, for example mineral oils, animal or vegetable fats, oils and waxes, or oils, waxes and fats based on synthetic esters (for example phthalates, adipates, phosphates or trimellitates), and mixtures of synthetic esters with mineral oils in any desired ratios by weight, such as are used, for example, as spinning dressings, and aqueous emulsions thereof.

29. Aqueous emulsions of natural or synthetic rubbers, for example natural rubber latex or latices of carboxylated styrene/butadiene copolymers.

The invention also relates, therefore, to compositions containing organic material and at least one compound of the formula I.

The organic materials are preferably the polymers defined above, particularly synthetic polymers, such as, for instance, thermoplastics (for example polyolefins or styrene copolymers) and elastomers. Polyolefins are particularly preferred, in particular polyethylene and polypropylene and copolymers thereof.

In general, the compounds according to the invention are added to the organic material to be stabilized in amounts of 0.01 to 10%, preferably 0.05 to 5%, especially 0.1 to 2%, relative to the total weight of the material to be stabilized. The stabilized polymer compositions of the invention can, in addition, also contain various conventional additives, such as the following:

1. ANTIOXIDANTS 1.1. Alkylated monophenols, for example 2,6-ditert.-butyl-4-methylphenol, 2-tert.-butyl-4,6-dimethylphenol, 2,6-ditert.-butyl-4-ethylphenol, 2,6-ditert.-butyl-4-n-butylphenol, 2,6-ditert.-butyl-4-i-butylphenol, 2,6-dicyclopentyl-4-methylphenol, 2-(α-methylcyclohexyl)-4,6-dimethylphenol, 2,6-di-octadecyl-4-methylphenol, 2,4,6-tri-cyclohexylphenol, 2,6-ditert.-butyl-4-methoxymethylphenol and 2,6-dinonyl-4-methylphenol.

1.2. Alkylated hydroquinones, for example 2,6-ditert.-butyl-4-methoxyphenol, 2,5-ditert.-butylhydroquinone, 2,5-ditert.-amylhydroquinone and 2,6-diphenyl-4-octadecyloxyphenol.

1.3. Hydroxylated thiodiphenyl ethers, for example 2,2'-thiobis-(6-tert.-butyl-4-methylphenol), 2,2'-thiobis-(4-octylphenol), 4,4'-thiobis-(6-tert.-butyl-3-methylphenol) and 4,4'-thiobis-(6-tert.-butyl-2-methylphenol).

1.4. Alkylidenebisphenols, for example 2,2'-methylenebis-(6-tert.-butyl-4-methylphenol), 2,2'-methylenebis-(6-tert.-butyl-4-ethylphenol), 2,2'-methylenebis-[4-methyl-6-(α-methylcyclohexyl)-phenol], 2,2'-methylenebis-(4-methyl-6-cyclohexylphenol), 2,2'-methylenebis-(6-nonyl-4-methylphenol), 2,2'-methylenebis-(4,6-ditert.-butylphenol), 2,2'-ethylidenebis-(4,6-ditert.-butylphenol), 2,2'-ethylidenebis-(6-tert.-butyl-4-isobutylphenol), 2,2'-methylenebis-[6-(α-methylbenzyl)-4-nonylphenol], 2,2'-methylenebis-[6-(α,α-dimethylbenzyl)-4-nonylphenol], 4,4'-methylenebis-(2,6-ditert.-butylphenol), 4,4'-methylenebis-(6-tert.-butyl-2-methylphenol), 1,1-bis-(5-tert.-butyl-4-hydroxy-2-methylphenyl)-butane, 2,6-bis-(3-tert.-butyl-5-methyl-2-hydroxybenzyl)-4-methylphenol, 1,1,3-tris-(5-tert.-butyl-4-hydroxy-2-methylphenyl)-butane, 1,1-bis-(5-tert.-butyl-4-hydroxy-2-methylphenyl)-3-n-dodecylmercaptobutane, ethylene glycol bis-[3,3-bis-(3'-tert.-butyl-4'-hydroxyphenyl)-butyrate], bis-(3-tert.-butyl-4-hydroxy-5-methylphenyl)-dicyclopentadiene and bis-[2-(3'-tert.-butyl-2'-hydroxy-5'-methylbenzyl)-6-tert.-butyl-4-methylphenyl]terephthalate.

1.5. Benzyl compounds, for example 1,3,5-tris-(3,5-ditert.-butyl-4-hydroxybenzyl)-2,4,6-trimethylbenzene, bis-(3,5-ditert.-butyl-4-hydroxybenzyl)sulfide, isooctyl 3,5-ditert.-butyl-4-hydroxybenzylmercaptoacetate, bis-(4-tert.-butyl-3-hydroxy-2,6-dimethylbenzyl)-dithiol terephthalate, 1,3,5-tris-(3,5-ditert.-butyl-4-hydroxybenzyl)isocyanurate, 1,3,5-tris-(4-tert.-butyl-3-hydroxy-2,6-dimethylbenzyl)isocyanurate, dioctadecyl 3,5-ditert.-butyl-4-hydroxybenzylphosphonate, the Ca salt of monoethyl 3,5-ditert.-butyl-4-hydroxybenzylphosphonate and 1,3,5-tris-(3,5-dicyclohexyl-4-hydroxybenzyl)isocyanurate.

1.6. Acylaminophenols, for example 4-hydroxylauranilide, 4-hydroxystearanilide, 2,4-bis-(octylmercapto)-6-(3,5-ditert.-butyl-4-hydroxyanilino)-s-triazine and octyl N-(3,5-ditert.-butyl-4-hydroxyphenyl)-carbamate.

1.7. Esters of β-(3,5-ditert.-butyl-4-hydroxyphenyl)-propionic acid with monohydric or polyhydric alcohols, for example methanol, octadecanol, 1,6-hexanediol, neopentylglycol, thiodiethylene glycol, diethylene glycol, triethylene glycol, pentaerythritol, tris-(hydroxyethyl)isocyanurate and N,N'-bis-(hydroxyethyl)-oxamide.

1.8. Esters of β-(5-tert.-butyl-4-hydroxy-3-methylphenyl)propionic acid with monohydric or polyhydric alcohols, for example methanol, octadecanol, 1,6-hexanediol, neopentylglycol, thiodiethylene glycol, diethylene glycol, triethylene glycol, pentaerythritol, tris-(hydroxyethyl)isocyanurate and N,N'-bis-(hydroxyethyl)-oxamide.

1.9. Esters of β-(3,5-dicyclohexyl-4-hydroxyphenyl)-propionic acid with monohydric or polyhydric alcohols, for example methanol, octadecanol, 1,6-hexanediol, neopentylglycol, thiodiethylene glycol, diethylene glycol, triethylene glycol, pentaerythritol, tris-(hydroxyethyl)isocyanurate and N,N'-bis-(hydroxyethyl)-oxamide.

1.10. Amides of β-(3,5-ditert.-butyl-4-hydroxyphenyl)-propionic acid, for example N,N'-bis-(3,5-ditert.-butyl-4-hydroxyphenyl-propionyl)-hexamethylenediamine, N,N'-bis-(3,5-ditert.-butyl-4-hydroxyphenylpropionyl)-trimethylenediamine and N,N'-bis-(3,5-ditert.-butyl-4-hydroxyphenylpropionyl)-hydrazine.

2. UV ABSORBERS AND LIGHT STABILIZERS 2.1. 2-(2'-hydroxyphenyl)-benzotriazoles, for example the 5'-methyl, 3',5'-ditert.-butyl, 5'-tert.-butyl, 5'-(1,1,3,3-tetramethylbutyl), 5-chloro-3',5'-ditert.-butyl, 5-chloro-3'-tert.-butyl-5'-methyl, 3'-sec.-butyl-5'-tert.-butyl, 4'-octoxy, or 3',5'-ditert.-amyl, or 3',5'-bis-(α,α-dimethylbenzyl) derivative.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy or 2'-hydroxy-4,4'-dimethoxy derivative.

2.3. Esters of substituted or unsubstituted benzoic acids, for example 4-tert.-butylphenyl salicylate, phenyl salicylate, octylphenyl salicylate, dibenzoylresorcinol, bis-(4-tert.-butylbenzoyl)-resorcinol, benzoylresorcinol, 2,4-ditert.-butylphenyl 3,5-ditert.-butyl-4-hydroxybenzoate and hexadecyl 3,5-ditert.-butyl-4-hydroxybenzoate.

2.4. Acrylates, for example ethyl or isooctyl α-cyano-β,β-diphenylacrylate, methyl α-carbomethoxycinnamate, methyl or butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis-[4-(1,1,3,3-tetramethylbutyl)-phenol], such as the 1:1 or 1:2 complex, if appropriate containing additional ligands, such as n-butylamine, triethanolamine or N-cyclohexyldiethanolamine, nickel dibutyldithiocarbamate, nickel salts of monoalkyl esters of 4-hydroxy-3,5-ditert.-butylbenzylphosphonic acid, such as the methyl or ethyl ester, nickel complexes of ketoximes, such as 2-hydroxy-4-methylphenyl undecyl ketone oxime, and nickel complexes of 1-phenyl-4-lauroyl-5-hydroxypyrazole, if appropriate containing additional ligands.

2.6. Sterically hindered amines, for example bis-(2,2,6,6-tetramethylpiperidyl)sebacate, bis-(1,2,2,6,6-pentamethylpiperidyl)sebacate, bis-(1,2,2,6,6-pentamethylpiperidyl) n-butyl-3,5-ditert.-butyl-4-hydroxybenzylmalonate, the condensation product formed from 1-hydroxyethyl-2,2,6,6-tetramethyl-4-hydroxypiperidine and succinic acid, the condensation product formed from N,N'-bis-(2,2,6,6-tetramethyl-4-piperidyl)-hexamethylenediamine and 4-tert.-octylamino-2,6-dichloro-1,3,5-s-triazine, tris-(2,2,6,6-tetramethyl-4-piperidyl)nitrilotriacetate, tetrakis-(2,2,6,6-tetramethyl-4-piperidyl) 1,2,3,4-butanetetraoate and 1,1'-(1,2-ethanediyl)-bis-(3,3,5,5-tetramethylpiperazinone). 2.7. Oxamides, for example 4,4'-dioctyloxyoxanilide, 2,2'-dioctyloxy-5,5'-ditert.-butyloxanilide, 2,2'-didodecyloxy-5,5'-ditert.-butyloxanilide, 2-ethoxy-2'-ethyloxanilide, N,N'-bis-(3-dimethylaminopropyl)-oxamide, 2-ethoxy-5-tert.-butyl-2'-ethyloxanilide and a mixture thereof with 2-ethoxy-2'-ethyl-5,4'-ditert.-butyloxanilide and mixtures of o-methoxy- and p-methoxy-disubstituted oxanilides and of o-ethoxy- and p-ethoxy-disubstituted oxanilides.

3. Metal deactivators, for example N,N'-diphenyloxamide, N-salicylal-N'-salicyloylhydrazine, N,N'-bis-(salicyloyl)hydrazine, N,N'-bis-(3,5-ditert.-butyl-4-hydroxyphenylpropionyl)-hydrazine, 3-salicyloylamino-1,2,4-triazole and bis-(benzylidene)-oxalic acid dihydrazide.

4. Phosphites and phosphonites, for example triphenyl phosphite, diphenyl alkyl phosphites, phenyl dialkyl phosphites, tris-(nonylphenyl)phosphite, trilauryl phosphite, trioctadecyl phosphite, distearyl pentaerythritol diphosphite, tris-(2,4-ditert.-butylphenyl)-phosphite, diisodecyl pentaerythritol diphosphite, bis-(2,4-ditert.-butylphenyl)pentaerythritol diphosphite, tristearyl sorbitol triphosphite, tetrakis-(2,4-ditert.-butylphenyl) 4,4'-biphenylenediphosphonite and 3,9-bis-(2,4-ditert.-butylphenoxy)-2,4,8,10-tetraoxa-3,9-diphosphaspiro[5.5]undecane.

5. Compounds which destroy peroxides, for example esters of β-thiodipropionic acid, for example the lauryl, stearyl, myristyl or tridecyl ester, mercaptobenzimidazole, the zinc salt of 2-mercaptobenzimidazole, zinc dibutyldithiocarbamate, dioctadecyl disulfide and pentaerythritol tetrakis-(β-dodecylmercapto)-propionate.

6. Polyamide stabilizers, for example copper salts in combination with iodides and/or phosphorus compounds and salts of divalent manganese.

7. Basic co-stabilizers, for example melamine, polyvinylpyrrolidone, dicyanodiamide, triallyl cyanurate, urea derivatives, hydrazine derivatives, amines, polyamides, polyurethanes and alkali and alkaline earth metal salts of higher fatty acids, for example Ca stearate, Zn stearate, Mg stearate, Na ricinoleate, K palmitate, antimony pyrocatecholate or tin pyrocatecholate.

8. Nucleating agents, for example 4-tert.-butylbenzoic acid, adipic acid and diphenylacetic acid.

9. Fillers and reinforcing agents, for example calcium carbonate, silicates, glass fibers, asbestos, talc, kaolin, mica, barium sulphate, metal oxides and hydroxides, carbon black and graphite.

10. Other additives, for example plasticizers, lubricants, emulsifiers, pigments, optical brighteners, fire-retarding agents, antistatic agents and blow agents.

The stabilizer substances according to the invention and, if necessary, further additives are incorporated into the organic material by known methods. This can, for example, be effected by mixing in the products according to the invention and, if appropriate, further additives by the methods customary in the art, before or during shaping, or by applying the compounds in a dissolved or dispersed form to the polymer, if appropriate with subsequent removal of the solvent by evaporation. The products according to the invention can also be added to the materials to be stabilized in the form of a masterbatch containing these compounds in a concentration of, for example, 2.5 to 25% by weight. The products according to the invention can also be added before or during polymerization or before crosslinking.

The materials thus stabilized can be used in a very wide variety of shapes, for example as films, fibers, tapes, molding compositions or profiles or as binders for paints, adhesives or putties.

For stabilizing organic material it can be advantageous to employ the compounds according to the invention together with so-called "peroxide destroyers", for example distearyl thiodipropionate.

The compounds of the formula I are also particularly advantageous processing stabilizers for low-density and high-density polyethylene.

The examples which follow illustrate the invention further. Here, as in the remainder of the description, all percentages are by weight, unless stated otherwise.

EXAMPLE 1

Preparation of 3,9-bis-[3',5'-bis-(3",5"-ditert.-butyl-4"-hydroxybenzyl)-2',4',6'-trimethylphenoxy]-2,4,8,10-tetraoxa-3,9-diphosphaspiro[5,5]undecane of the formula

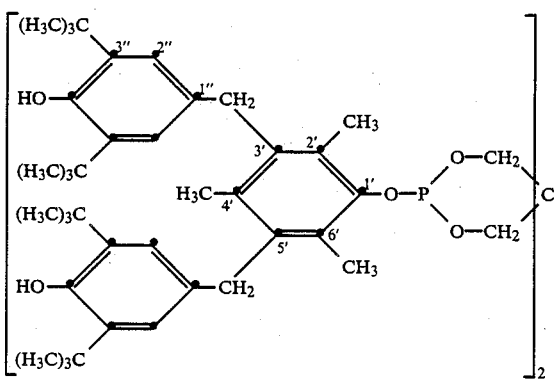

57.28 g (0.1 mol) of 3,5-bis-[3',5'-ditert.-butyl-4'-hydroxybenzyl]-2,4,6-trimethylphenol and 57.7 g of triethylamine in 300 ml of xylene are added dropwise in the course of 10 minutes and at a temperature between 5° and 10° C., to a solution of 13.25 g (0.05 mol) of 3,9-dichloro-2,4,8,10-tetraoxa-3,9-diphosphaspiro[5,5]undecane in 30 ml of xylene. The reaction mixture is stirred for 21 hours at room temperature. The insoluble constituents are then filtered off and the filtrate is evaporated to dryness. This gives 57.5 g of a colourless product having a melting point of 246° C.

Elementary analysis: Calculated: P 4.63% Found: P 4.48%

EXAMPLE 2

Preparation of 2-[3',5'-bis(3",5"-ditert.-butyl-4"-hydroxybenzyl)-2',4',6'-trimethylphenoxy]-5,5-dimethyl[1,3,2]dioxaphosphinane of the formula

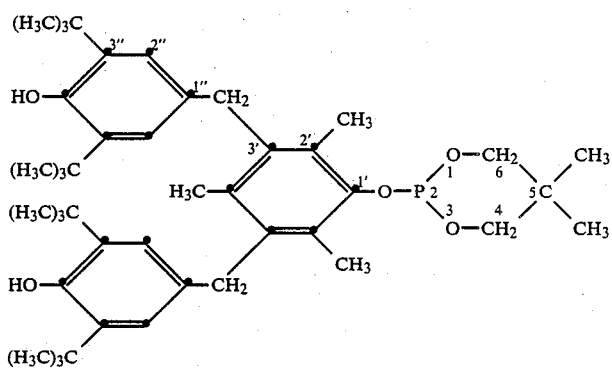

A solution of 8.45 g of 2-chloro-5,5-dimethyl[1,3,2]dioxaphosphinane in 50 ml of toluene is added dropwise, in the course of 15 minutes and at a temperature between 20° and 30° C., to a solution of 28.65 g of 3,5-bis-[3',5'-ditert.-butyl-4'-hydroxybenzyl]-2,4,6-trimethylphenol and 25.3 g of triethylamine in 150 ml of toluene. The reaction mixture is heated under reflux for 24 hours. After cooling to room temperature, the residue is filtered off and the filtrate is evaporated to dryness. This gives 35 g of a colourless product having a melting point of 190° C.

Elementary analysis: Calculated: P 4.39% Found: P 4.31%

EXAMPLE 3

Preparation of
2-[3',5'-bis(3'',5''-ditert.-butyl-4''-hydroxybenzyl)-2',4',6'-trimethylphenoxy]-2,4,8,10-tetratert.-butyl-dibenzo[d,g][1,3,2]dioxaphosphocin of the formula

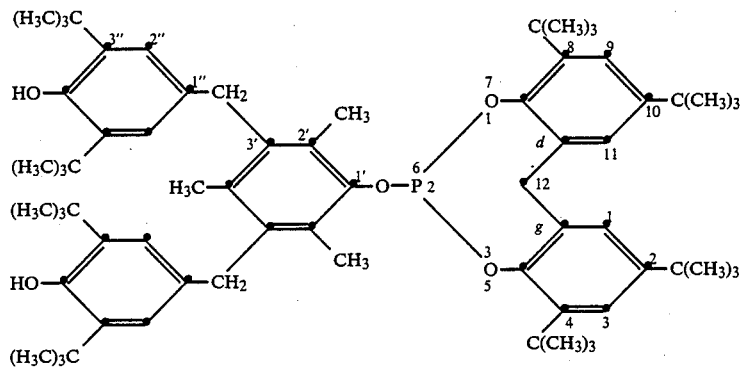

The preparation is carried out analogously to Example 2. 12.23 g of 2-chloro-2,4,8,10-tetratert.-butyldibenzo[d,g][1,3,2,]dioxaphosphocin are employed as the chlorophosphite. Purification by column chromatography gives 18.54 g of a colourless powder having a melting point of 136° C.

Elementary analysis: Calculated: P 3.02% Found: P 2.89%

EXAMPLE 4

Preparation of
2-[3',5'-bis(3'',5''-ditert.-butyl-4''-hydroxybenzyl)-2',4',6'-trimethylphenoxy]-4,8-ditert.-butyl-2,10-dimethyl-dibenzo[d,g][1,3,2]dioxaphosphocin of the formula

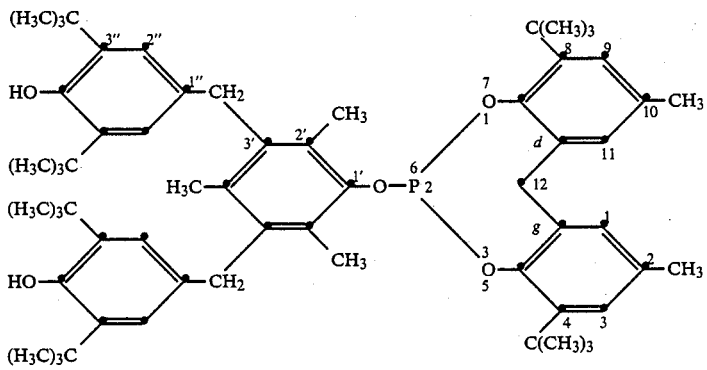

The preparation is carried out analogously to Example 2. 10.12 g of 2-chloro-4,8-ditert.-butyl-2,10-dimethyldibenzo[d,g][1,3,2]dioxaphosphocin are employed as the chlorophosphite. Purification by column chromatography gives a product consisting of 10 g of a colourless powder having a melting point of 127° C.

Elementary analysis: Calculated: P 3.29% Found: P 3.37%

EXAMPLE 5

Preparation of
tris-[3,5-bis-(3',5'-ditert.-butyl-4'-hydroxybenzyl)-2,4,6-trimethylphenyl]phosphite of the formula

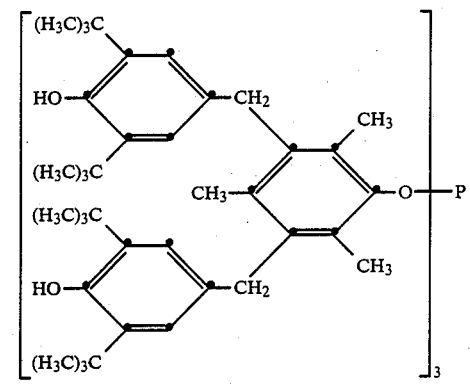

A solution of 4.1 g (0.03 mol) of phosphorus trichloride in 100 ml of toluene is added dropwise, in the course of 60 minutes and at a temperature between 0° and 5° C., to a solution of 51.6 g (0.09 mol) of 3,5-bis-(3',5'-ditert.-butyl-4'-hydroxybenzyl)-2,4,6-trimethylphenol in 250 ml of toluene and 9.1 g of triethylamine. The reaction mixture is stirred for 16 hours at 70° C. The insoluble constituents are filtered off at room temperature and the filtrate is evaporated to dryness. The residue is taken up in 500 ml of 1:1 toluene/hexane, the solution is filtered and the filtrate is again evaporated to dryness. This gives 52 g of a colourless powder having a melting point of 255°–257° C.

Elementary analysis: Calculated: P 1.77% Found: P 1.70%

EXAMPLE 6

Polypropylene powder (melt flow index at 230° C. and under an applied load of 2.16 kp: 2.3 g/10 minutes) containing 0.1% of calcium stearate is mixed with the additives listed in Tables 1 and 2 below and is then kneaded in a Brabender plastograph at 200° C. for 10 minutes. The composition thus obtained is compressed in a press having a surface temperature of 260° C. to give sheets 1 mm thick, from which strips 1 cm wide and 6.5 cm long are punched out. Several strips of this type from each sheet are hung in a circulating air oven heated at 135° C. and 149° C. and are inspected at regular intervals. The oxidative decomposition of these strips can be recognized by a yellow discoloration which starts as a circular spot. The time required for decomposition is a measure of the stability of the sample.

TABLE 1

| Stabilizer | Days in the circulating air oven until the test specimen decomposes | |
|---|---|---|
| | 135° C. | 149° C. |
| None | <1 | <1 |
| 0.2% of the compound from Example 1 | 58 | 18 |
| 0.2% of the compound from Example 2 | 56 | 15 |
| 0.2% of the compound from Example 3 | 69 | 16 |
| 0.2% of the compound from Example 4 | 69 | 16 |
| 0.2% of the compound from Example 5 | 71 | 20 |

TABLE 2

| Stabilizer | Days in the circulating air oven until the test specimen decomposes | |
|---|---|---|
| | 135° C. | 149° C. |
| 0.1% of the compound from Example 5 + 0.3% of distearyl thiodipropionate | 195 | 47 |

What is claimed is:

1. a compound of formula I

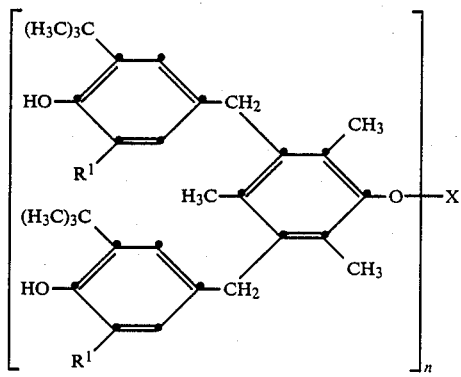

in which
n is 1, 2 or 3,
$R^1$ is $C_1-C_4$-alkyl or cyclohexyl,
when n is 1, X is a group of formula II or III

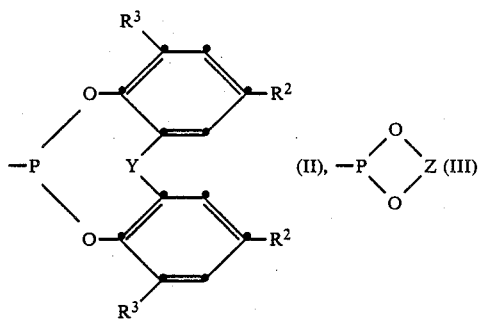

in which
$R^2$ and $R^3$ independently of one another are $C_1-C_4$-alkyl, or $R^3$ is additionally cyclohexyl,
Y is —S—, —$CH_2$— or —CH($C_1-C_4$-alkyl)—, and
Z is a 1,3-alkylene group which has 4 to 8 carbon atoms and is branched in the 2-position,
when n is 2, X is a group of formula IV

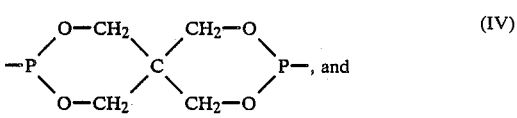

when n is 3, X is a phosphorus atom.

2. A composition of matter containing a synthetic polymer subject to thermo-oxidative and/or light-induced degradation, stabilized with an effective stabilizing amount of a compound according to claim 1.

3. A compound of the formula I according to claim 1, in which n is 1 or 2.

4. A compound of the formula I according to claim 1, in which $R^1$ is tert.-butyl.

5. A compound according to claim 1 wherein $R^1$ is methyl or tert-butyl.

6. A compound according to claim 1 wherein, when n is 1, X is a group of formula II.

7. A compound according to claim 1 wherein Y is —S—, —$CH_2$— or —$CHCH_3$—.

8. A compound according to claim 1 wherein $R^2$ and $R^3$ are independently $C_1-C_4$-alkyl and Y is —$CH_2$—.

9. The compound which is 3,9-bis-[3',5'-bis(3'',5''-ditert.-butyl-4''-hydroxybenzyl)-2',4',6'-trimethylphenoxy]-2,4,8,10-tetra-oxa-3,9-diphosphaspiro[5,5]undecane, 2-[3',5'-bis(3'',5''-ditert.-butyl-4''-hydroxybenzyl)-2',4',6'-trimethylphenoxy]-5,5-dimethyl-[1,3,2]dioxaphosphinane, 2-[3',5'-bis(3'',5''-ditert.-butyl-4''-hydroxybenzyl)-2',4',6'-trimethylphenoxy]-2,4,8,10-tetratert.-butyl-dibenzo[d,g][1,3,2]dioxaphosphocin, 2-[3',5'-bis(3'',5''-ditert.-butyl-4''-hydroxybenzyl)-2',4',6'-trimethylphenoxy]-4,8-ditert.-butyl-2,10-dimethyl-dibenzo-[d,g][1,3,2]dioxaphosphocin or tris[3,5-bis(3',5'-ditert.-butyl-4'-hydroxybenzyl)-2,4,6-trimethylphenyl]phosphite according to claim 1.

10. A composition according to claim 2, in which the synthetic polymer is a polyolefin.

11. A method for stabilizing a synthetic polymer against thermo-oxidative and/or light-induced degradation, which comprises incorporating into said synthetic polymer an effective stabilizing amount of a compound according to claim 1.

* * * * *